United States Patent [19]

Wiersma

[11] Patent Number: 5,753,493

[45] Date of Patent: May 19, 1998

[54] EGG WASHING DECONTAMINATION PROCESS

[75] Inventor: Jack G. Wiersma, Jupiter, Fla.

[73] Assignee: Nouveau Technologies, Inc., Tequesta, Fla.

[21] Appl. No.: 619,918

[22] Filed: Mar. 20, 1996

Related U.S. Application Data

[63] Continuation-in-part of Ser. No. 602,232, Feb. 15, 1996.
[51] Int. Cl.$^6$ .............. C12N 1/02; A21D 4/00; C11D 17/00
[52] U.S. Cl. .............. 435/261; 510/417; 426/326
[58] Field of Search .............. 435/261; 424/405; 426/326, 320, 335; 451/903; 210/643; 510/417; 585/514

[56] References Cited

U.S. PATENT DOCUMENTS

| | | | |
|---|---|---|---|
| 3,719,590 | 3/1973 | Li et al. | 585/818 |
| 3,968,250 | 7/1976 | Boucher | 514/705 |
| 3,992,146 | 11/1976 | Fazzalari | 422/29 |

FOREIGN PATENT DOCUMENTS

| | | |
|---|---|---|
| 06133741 | 5/1994 | Japan. |
| 95/04126 | 2/1995 | WIPO. |

*Primary Examiner*—Jean C. Witz
*Assistant Examiner*—Susan Hanley
*Attorney, Agent, or Firm*—McHale & Slavin

[57] ABSTRACT

The instant invention is an egg wash decontaminating solution and process. The decontaminating solution and process allows for reducing the surface tension of a biofilm allowing for the removal of the biofilm and control of underlying bacteria. A solution of triterpene saponin provides the surface tension wherein an optional soft acid such as food grade sodium lactate operates to control the bacteria. The saponin further acts as a foaming agent providing visual indication of operation while holding matter in suspension.

7 Claims, No Drawings

EGG WASHING DECONTAMINATION PROCESS

Field of the Invention:

This invention relates to the decontamination of bacteria laden surfaces and in particular to a saponin formulation and process for commercial egg washing.

BACKGROUND OF THE INVENTION

This is a Continuation-in-Part of U.S. Patent Application entitled Decontamination Process having Ser. No. 08/602232, filed Feb. 15 1996, the contents of which are incorporated herein by reference as if fully restated.

Bacteria is a group of microscopic, unicellular organisms that lack a distinct nucleus and reproduce by cell division. Bacteria typically range from 1 to 10 micrometers and vary in the ways they obtain energy and nourishment. About 200 species of bacteria are pathogenic, pathogenicity varies among the species and is dependent on both the virulence of the species and the condition of the host organism. The $E.$ $coli$ 0157:H7 and salmonella microorganisms are just two of the most well known pathogenic bacteria which may cause death in humans.

It is well known that bacteria is involved in the spoilage of dairy products, namely eggs, to which this invention is directed. Bacteria may actually render such foods unpalatable by changing their composition. Bacteria growth can also lead to food poisoning such as that caused by clostridium botulinum or $Staphylococcus$ $aureus$.

Bacteria can be aerobes or anaerobes and are capable of attaching to any surface. Under certain conditions, especially in egg production, bacteria can quickly form a microorganism which seeks a solid surface having nutrients for growth. As the microorganisms grow and multiply, the newly formed cells attach to each other as well as to the surface forming a confluent colony. When the colony becomes sufficiently large, it entraps debris, nutrients, and other microorganisms, wherein a microbial biofilm is established. A biofilm coating enhances the ability of bacteria to resist removal and inactivation. If a biofilm conceals a pathogenic bacteria, the result can lead to illness and death if the bacteria is later introduced to a human.

According to industry publications presented by Characklis and Cooksel in 1983 further supplemented by Characklis in 1984, set forth in Food Technology, Article of July 1994, Volume 48, No. 7, the biofilm is considered a five stage process which results from the physical, chemical and biological phenomenon and is identified as follows: transport of nutrients, inorganic, and organic matter to the solid surface; absorption of a conditioning film containing inorganic or organic nutrients; attachment of microbial cells to the wetted surface in initiation of growth; Bacterial metabolism within the biofilm; and cell disruption and detachment from the biofilm.

For these reasons, efforts are constantly under way to discover an economical and safe method for the destruction of bacteria. The problem is that the protective coating made by the biofilm requires treatment strong enough to break through the biofilm, destroy the underlying bacteria, yet not harm or alter the treated product. Common knowledge states that an emphasis must be placed on proper cleaning and sanitizing procedures, such as that provided through egg washing upon production of the eggs.

The cleaning of eggs in a commercial setting is required to remove the contaminants from the surface of an egg shell. Until cleaned, the shell is a known breeding ground for various types of bacteria, the most notorious of which is the salmonella enderitidis. An egg effectively has four layers. The cuticle is a thin layer of hard protective coating followed by a thick layer of calcium carbonate which forms the shell, but is also porous. Beneath the calcium carbonate shell is two membranes which are porous, thereby relying on the cuticle to be the main barrier to prevent bacteria from entering into the egg from the porous openings of the shell and the two inner membranes. The cuticle can quickly provide a basis for a biofilm unless otherwise treated.

A common chemical used in egg washing is based upon an alkaline solution which has recently been reported by the Food Safety Consortium as resulting in an egg shell that is 30 to 70 times more porous than egg shells washed with other chemical washes. Egg washing performed at high pH, such as with alkaline trisodium phosphate (tsp) results in flaking of the cuticle and at higher concentrations actually removes the cuticle from the shell. Even if the higher concentration of chemical kills bacteria, when the eggs are inoculated pathogens may then penetrate the once disinfected shells more easily should the cuticle be destroyed.

Other egg washing constituents such as quaternary ammonium compounds having a pH of 7.5, sodium carbonate having a pH of 12, sodium hydroxide having a pH of 12.5 and sodium hypochloride having a pH of 7.5 all show effective kill against salmonella, although the higher pH concentrations are harsh enough to damage or remove whole cuticle layers. The lower pH is known to provide an effective kill of the bacteria with minimal damage to the cuticle.

Another problem with chemical egg wash solutions of the prior art is that the resulting noxious compounds which may contaminate the environment and in most instances regulations require that egg wash water is neutralized and disposed off site.

Thus, what is lacking in the art is an egg washing solution and process that does not effect shell strength or utilize noxious chemicals. In addition, what is needed is an egg washing solution and process that effectively removes bacteria using a natural and biodegradable process.

SUMMARY OF THE INVENTION

The instant invention is a decontamination solution consisting of a saponin base having a particular application for use in egg washing for removal of dirt and bacterial contamination. The solution is a colloidal emulsion employing triterpene saponin within a formulation that, when applied under certain conditions, is capable of reducing the surface tension of a biofilm allowing for removal and control of underlying bacteria. Triterpene saponin is non-steroidal and commercially available. The saponin operates as a foaming agent, emulsifier, and provides surface tension reduction capable of loosening dirt, contaminates, and a biofilm that forms on the cuticle of an egg shell. When the biofilm is removed, a biocide such as sodium lactate acid can be optionally employed to inhibit bacteria growth.

Because the molecular structure of the triterpene saponin is colloidal, it does not penetrate the surface of an egg shell. Triterpene saponin is slightly acidic having a pH of between 4 and 5 thereby maintaining shell integrity. It has been observed that a synergism takes place in creating the emulsion and should a bacterial inhibitor be desired, allow for a reduced amount of such inhibitor such as lactate acid to be used and that a stable, controllable exposure for the acid to contact the bacteria is achieved. At the same time the loosening or stripping away of the biofilm is made possible.

In addition, it has been found that increasing the temperature of the solution to between 110° F. and 115° F. enhances the process.

When applied to an egg shell surface, the solution remains on the surface from 10 to 30 seconds, the emulsion begins loosening or stripping away the biofilm. As the biofilm is removed, a soft acid may be placed in the solution which allows direct contact with the associated bacteria located on the biofilm, as well as beneath the biofilm providing exposure time for the destruction of bacteria. Exposure time is critical since the acid requires contact time for effective destruction of bacteria. The amount of contact time required depends upon the type of bacteria that is treated.

The process consists of preparing a recyclable solution used in rinsing of raw eggs. A typical recycling solution consists of about 50 ml of 50% saponin placed into approximately 150 gallons of heated water in a first holding container. The raw eggs are then coated with the heated saponin solution for at least a 10 second contact time. The excess saponin solution is returned through said first holding container providing a decontamination solution for approximately 8 hours of treatment. The decontamination process treats approximately 30,000 eggs per hour by removal of a biofilm from the cuticle layer of an egg shell. In addition, it has been found that an additional 50 ml of 50% saponin should be placed into the holding tank after the first hour. The process may include the step of adding a solution of sodium lactate or copper sulfate pentahydrate for bacteria control.

The saponin solution provides a white foam which allows for visual verification of sufficient solution strength for operation. In addition, unlike the yellowish color of conventional egg wash solution, the saponin based solution is white allowing yet another visual indicator of cleaning solution contamination.

Thus, an objective of this invention is to simplify current egg decontamination processes by teaching the use of a concentrated emulsion formulation capable of reducing the surface tension of biofilms associated with raw eggs for subsequent removal.

Another objective of this invention is to teach a decontamination solution and process that is economical, simple to apply, and environmentally friendly.

Still another objective of the instant invention is to provide a cleaning solution that permits run-off with the benefit of cleaning the underlying surface.

Another objective of the invention is to provide the consumer with a bright white foam solution providing visual indication of solution strength.

Another objective of the instant invention is to provide an egg washing material that is biodegradable and can be disposed of on-site.

Yet still another objective of the instant invention is to provide a solution for egg washing whose concentration can be visually viewed in relation to the foam concentrate.

Still another objective of the instant invention is to provide a concentrated egg washing solution that requires less storage space than conventional egg washing chemicals.

Other objects and advantages of this invention will become apparent from the following description wherein are set forth, by way of illustration and example, certain embodiments of this invention.

DETAILED DESCRIPTION OF THE PREFERRED EMBODIMENT

Saponins are naturally occurring oily glycosides that foam freely when shaken with water. They occur in a wide variety of plants including acacia, soapwort, soaproot, California pigweed, and many others. The use of a triterpene saponin, commonly referred to as Saponin Departum Levissium Q, is non-steroidal and commercially available. The preferred embodiment of this invention is directed to the triterpene saponin, yet it will be obvious to one of ordinary skill in the art that the various types of saponins may be substituted leading to various levels of success. Unique to the saponin is its ability to operate as a foaming agent and emulsifier leading to surface reduction capabilities. An artificial reproduction of saponin is deemed within the scope of this invention.

Biofilms are known to have a surface tension which acts in a direction parallel to the boundary surface. Water, possessing powerful intermolecular attractive forces, has a high surface tension (72.8 dynes/cm at 20° C). Many soluble surfaces, mainly organic, when dissolved in water reduce the surface tension even when added in very low concentrations. The inventor has discovered that the incorporation of triterpene saponin, when based on a 5% aqueous solution results in a surface tension of 44.5 dynes/cm.

The instant invention is a colloidal emulsion employing saponin capable of reducing the surface tension of a biofilm allowing for the removal and control of bacteria. The triterpene saponin solution is environmentally safe, non-steroidal, and makes a foaming agent and emulsifier capable of reducing surface tension for loosening of the biofilm.

It is recognized that the loosening of or the stripping away of the biofilm in and of itself will not render the product completely bacteria free, therefore a optional additive to the product would be a soft acid, such as a lactate acid. Sodium lactate is preferred, as the USDA allows the use of sodium lactate in meat and poultry products up to 2% of the formulation under 9 CFR 319.180. Sodium lactate 60% food grade is a commercially available lactate acid and can be combined with the saponin for effective bacterial control.

As previously mentioned, the saponin used in the creation of this emulsion are colloidal. The colloidals are thus intermediate between core suspensions on the one hand and molecular or ionic solutions on the other. Because the molecular structure of the triterpene saponin is colloidal, it does not penetrate the surface of the material being treated. The triterpene saponin used in this emulsion has a pH between 4 and 5 and it is noted that a synergism takes place in creating the emulsion by allowing a reduced amount of lactate acid to be used, while at the same time the loosening or stripping away of the biofilm is made possible.

When applied to a surface, such as an egg shell, and the solution remains on the surface from 10 to 30 seconds, the foam containing the emulsion begins loosening or stripping away the biofilm. As the biofilm is removed a soft acid can be used which provides a direct contact with the associated bacteria located on the biofilm, as well as beneath the biofilm, providing exposure time for the destruction of bacteria. Exposure time is critical if acid is used for destruction of bacteria. The amount of contact time required depends upon the type of bacteria that is treated.

In a preferred operation, the eggs are rinsed through a recycling system by admixing about 50 ml of 50% saponin with approximately 150 gallons of heated water in a first holding container; coating raw eggs with said heated saponin solution for at least 10 seconds contact time; and recycling saponin solution coating said raw eggs through said first holding container providing a decontamination solution for approximately 8 hours of treatment. The decontamination process treats approximately 30,000 eggs per hour by removal of a biofilm from the cuticle layer of an egg shell. The process may include the step of adding a solution of sodium lactate to said solution.

Thus, an egg washing solution for cleaning and decontaminating eggs prior to commercial distribution would consist of a saponin for reducing the surface tension of a biofilm formed on the cuticle layer of an egg shell; and a contact means for maintaining said reducing means against said biofilm. Preferably the egg washing solution is triterpene saponin and optionally includes a bactericide such as copper sulphate pentahydrate or a soft acid lactate acid.

A comparison test was performed against a conventional chemical egg wash solution consisting of sodium carbonate, sodium hydroxide, sodium tripolyphosphate, sodium meta silicate, and a poloxamer, the results of the test set forth in Chart 1. Over an eight hour day of production with a washing of approximately 200 to 240 thousand eggs. The eggs are delivered through a 150 gallon recycling container which is emptied at the end of the day and if made of the conventional chemical constituents, must be transported off-site to an approved recycling location. A second container of 150 gallons is used for rinsing of the eggs, the rinse water is recycled in a similar manner as the process water.

Wherein a triterpene saponin solution is provided in dosages over a period of time to treat a production of eggs for removal of dirt and bacterial contamination, the same if not lower bacterial counts were obtained. In Table 2, the results are set forth of a saponin concentrate consisting of a solution of triterpene saponin, wherein 90 ml of a 50% concentrate is added during a first hour, 90 ml is added during a second hour, and 120 ml is added during a third hour with the addition of 10 ml copper sulfate pentahydrate. In this trial, the water temperature was maintained at approximately 96° C. The actual results are set forth as follows:

TABLE 1

|  | Pre Wash 20 Eggs 10:30 am | Pre Wash 20 Eggs 3:00 pm | Post Wash 57 Eggs 10:30 am | | | Post Wash 58 Eggs 3:30 pm | | |
|---|---|---|---|---|---|---|---|---|
| Sample# | TNC* | TNC | 21 | 14 | 16 | 15 | 9 | 31 |
|  | TNC | TNC | 38 | 4 | 15 | 7 | 8 | 14 |
|  | TNC | TNC | 13 | 2 | 5 | 6 | 6 | 6 |
|  | TNC | TNC | 7 | 4 | 20 | 15 | 10 | 12 |
|  | TNC | TNC | 3 | 9 | 17 | 9 | 38 | 9 |
|  | TNC | TNC | 13 | 7 | 15 | 41 | 4 | 7 |
|  | TNC | TNC | 6 | 5 | 12 | 6 | 5 | 15 |
|  | TNC | TNC | 2 | 10 | 17 | 5 | 16 | 11 |
|  | TNC | TNC | 6 | 6 | 9 | 10 | 26 | 9 |
|  | TNC | TNC | 44 | 6 | 13 | 9 | 8 | 31 |
|  | TNC | TNC | 50 | 13 | 3 | 6 | 5 | 31 |
|  | TNC | TNC | 7 | 26 | 18 | 13 | 3 | 16 |
|  | TNC | TNC | 28 | 13 | 14 | 7 | 19 | 10 |
|  | TNC | TNC | 31 | 47 | 8 | 14 | 13 | 9 |
|  | TNC | TNC | 6 | 11 | 9 | 12 | 12 | 15 |
|  | TNC | TNC | 24 | 25 | 5 | 10 | 5 | 26 |
|  | TNC | TNC | 2 | 5 | 10 | 2 | 24 | 3 |
|  | TNC | TNC | 4 | 10 | 10 | 3 | 7 | 10 |
|  | TNC | TNC | TNC | TNC | TNC | 8 | 12 | 9 |
|  | TNC | TNC | 738 Colonies | | | TNC | | |
|  | TNC 20/20 | TNC 20/20 | 738 + 54 = 14 3/57 TNC | | | 702 Colonies 702 + 57 = 12 1/50 | | |

*TNC: Colonies too numerous to count.

TABLE 2

|  | Pre Wash 20 Eggs 10:30 am | Pre Wash 20 Eggs 3:00 pm | Post Wash 57 Eggs 10:30 am | | | Post Wash 58 Eggs 3:30 pm | | |
|---|---|---|---|---|---|---|---|---|
| Sample# | TNC* | TNC | 11 | 13 | 8 | 18 | 17 | 6 |
|  | TNC | TNC | 16 | 8 | 12 | 6 | 10 | 5 |
|  | TNC | TNC | 16 | 28 | 13 | 5 | 4 | 5 |
|  | TNC | TNC | 39 | 35 | 5 | 21 | 8 | 2 |
|  | TNC | TNC | 8 | 16 | 12 | 7 | 4 | 17 |
|  | TNC | TNC | 10 | 23 | 11 | 14 | 3 | 4 |
|  | TNC | TNC | 7 | 8 | 4 | 7 | 14 | 33 |
|  | TNC | TNC | 10 | 6 | 14 | 36 | 4 | 3 |
|  | TNC | TNC | 7 | 4 | 6 | 16 | 18 | 7 |
|  | TNC | TNC | 15 | 1 | 4 | 26 | 1 | 15 |
|  | TNC | TNC | 5 | 10 | 3 | 17 | 4 | 6 |

TABLE 2-continued

| Pre Wash 20 Eggs 10:30 am | Pre Wash 20 Eggs 3:00 pm | Post Wash 57 Eggs 10:30 am | | | Post Wash 58 Eggs 3:30 pm | | |
|---|---|---|---|---|---|---|---|
| TNC | TNC | 5 | 0 | 38 | 3 | 14 | 14 |
| TNC | TNC | 9 | 13 | 21 | 23 | 5 | 8 |
| TNC | TNC | 15 | 12 | 9 | 5 | 9 | 23 |
| TNC | TNC | 19 | 1 | 10 | TNC | TNC | TNC |
| TNC | TNC | 7 | 17 | 6 | TNC | TNC | TNC |
| TNC | TNC | 10 | 11 | 10 | TNC | TNC | TNC |
| TNC | TNC | 21 | 10 | 17 | TNC | TNC | TNC |
| TNC | TNC | 13 | 4 | 8 | TNC | TNC | TNC |
| TNC | TNC | 674 Colonies | | | TNC | | |
| TNC 20/20 | TNC 20/20 | 674 + 57 = 12 0/57 TNC | | | 462 Colonies 462 + 42 = 11 16/58 TNC | | |

*TNC: Colonies too numerous to count.

The TNC count at the end of the run on Table 2 was due to equipment malfunction. However, these test results are set forth as they are part of an elaborate verifiable study and even with the equipment failure, demonstrate that the saponin solution equals or exceeds the use of a conventional egg washing material without the noxious constituents.

Preferably the solution is based upon 150 gallons of recycled water with the temperature of the water maintained at approximately 110° to 115° F. with product usage of 50 ml for the first hour and 50 ml during the second hour. Product usage based upon 50% triterpene saponin. In addition, a percentage of sodium lactate 60% food grade level is added to the solution. It is noted that water temperature has a positive effect of the foaming capacity of the triterpene saponin in foam life even though there is no significant difference as to performance with the enhanced temperature. Thus, the higher temperature of approximately 110° to 115°F., allows a longer foam life thereby providing a visual indication of continuing operation of the triterpene saponin and further allowing the consumer to use less material as the amount of foam is a direct indication as to the amount of strength.

It should be noted that with conventional chemical solutions, chemical must be added every hour during an eight hour production resulting in higher administrative costs. The triterpene saponin need only be added twice during the first and second hours thereby decreasing the amount of employee time in maintaining the solution.

It is contemplated that any current foaming system can be used in a situation where the process calls for decontamination. In addition, a residual foam continues to suspend the biofilm. In an egg washing process, after the eggs are spray rinsed the removed emulsion continues to maintain the micro organisms in a suspended state. The suspended state continues as the solution falls to the processing floor and continues to work in cleaning of the floor or any other surface that the emulsion contacts while the foam is present. This operates to reduce the possibility of cross contamination and allows an entire processing room to be cleaned without the need for testing compatibility of cross decontamination products.

It is noted that the compatibility between the saponin or other foaming agents and optional acids should fall in a pH range of 4 to 10 allowing the emulsion to maintain its foaming properties. However, the higher pH range may lead to softer shells as with the conventional egg washing chemicals. This allows a wide variety of foaming agents and cleaning agents to be used. The compatibility of the key substances used in the development of the emulsion can be testing as follows further allowing for the testing of alternatives:

a. Add 300ml to a laboratory beaker using tap water. It should be noted that the tap water is considered to be potable wherein abnormal levels of chlorine or high dissolved solids will adversely affect the emulsion.

b. Add 5cc of sodium lactate 60% food grade to the beaker.

c. Add 10 cc of triterpene saponin to the beaker.

d. The solution is shaken until a heavy foam is created which will create a foam approaching the top of the beaker. The beaker can then be unsealed and observed at fifteen minute intervals over a period of one hour. The foam will remain stable with only minor reduction in foam volume nearing the top of the beaker. In this manner, the compatibility of the sodium lactate and the triterpene emulsion is tested for compatibility in a foam state. The same procedure performed without the sodium lactate will provide the same foaming action so as to verify that the soft acid used does not have an adverse affect on the ability of the triterpene saponin to perform.

It is to be understood that while a certain form of the invention is illustrated, it is not to be limited to the specific constituents or method of application herein described and shown. It will be apparent to those skilled in the art that various changes may be made without departing from the scope of the invention.

What is claimed is:

1. A process for decontaminating raw eggs wherein a biofilm is removed from the cuticle layer of the shells of said eggs comprising:

a) admixing about 50 mL of 50% saponin concentrate with heated water in a holding container to make a saponin solution wherein said solution is recycled and kept at a temperature between 110° and 115° F.;

b) coating raw eggs with the recycled saponin solution of step a) for at least 30 seconds to make saponin-coated eggs;

c) rinsing said saponin-coated eggs with water;

d) collecting any excess saponin solution from step b) and adding said excess solution to the holding container of step a) to make a recycled saponin solution; and e) disposing said recycled saponin solution after about 8 hours of said process for decontaminating said eggs.

2. The process of claim 1, wherein the saponin solution of step a) comprises a bacteriocidal amount of sodium lactate.

3. The process of claim 1, wherein the pH of the saponin solution is between 4 and 10.

4. The process of claim 1, wherein the temperature of the heated water is between 110° and 115° F.

5. The process of claim 1, wherein the saponin is a triterpene.

6. The process of claim 1, further comprising the step of admixing about 50 mL of 50% saponin concentrate with the heated recycled saponin solution of step a) after about 1 hour of the start of said decontamination process.

7. The process of claim 1, wherein approximately 30,000 raw eggs are decontaminated per hour and said holding container holds about 150 gallons of heated water.

* * * * *